United States Patent
Fader (10) Patent No.: US 6,548,744 B1
(45) Date of Patent: Apr. 15, 2003

(54) REDUCTION OF BOWMAN-BIRK PROTEASE INHIBITOR LEVELS IN PLANTS

(75) Inventor: Gary M. Fader, Landenberg, PA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/372,407

(22) Filed: Aug. 11, 1999

Related U.S. Application Data (60) Provisional application No. 60/097,450, filed on Aug. 21, 1998.

(51) Int. Cl.[7] .............................. A01H 1/00; A01H 5/00; C12N 5/04; C12N 15/82
(52) U.S. Cl. ...................... 800/298; 800/278; 800/286; 800/312; 800/320; 800/320.2; 800/320.3; 435/415; 435/410; 435/468
(58) Field of Search .................................. 800/290, 298, 800/312, 278, 320.3, 320.2, 320, 286; 536/23.1, 23.6; 435/419, 440, 468, 69.1, 415, 410

(56) References Cited

PUBLICATIONS

Broun et al., Catalytic Plasticity of Fatty Acid Modification Enzymes Underlying Chemical Diversity of Plant Lipids, Nov. 13, 1998, Science, vol. 282, pp. 1315–1317.*

Lazar et a., Transforming Growth Factor x: Mutation of Aspartic Acid 47 and Leucine 48 Results in Different Biological Activities, Mar. 1988, Molecular ad Cellular Biology, vol. 8, No. 3, pp. 1247–1252.*

Burgess et al., Possible Dissociation of the Heparin–binding and Mitogenic Activites of Heparin–binding ( Acid Fibroblast) . . . , 1990, The Journal of Cell Biology, vol. 111, pp. 2129–2138.*

Bowie et al., Deciphering the Message on Protein Sequences: Toletance to Amino Acid Substitutions, Mar. 16, 1990, vol. 247, pp. 1306–1310.*

Taylor et al., Plant Cell, vol. 9:1245–1249, Aug. 1997, Comprehending Cosuppression.

* cited by examiner

Primary Examiner—Elizabeth F. McElwain
Assistant Examiner—Stuart Baum (57) ABSTRACT

A method for reducing Bowman-Birk protease inhibitor levels in plants using either co-suppression or antisense technology is disclosed.

9 Claims, 3 Drawing Sheets

SEQUENCE LISTING

<160> NUMBER OF SEQ ID NOS: 4

<210> SEQ ID NO 1
<211> LENGTH: 28
<212> TYPE: DNA
<213> ORGANISM: Artificial Sequence
<220> FEATURE:
<223> OTHER INFORMATION: Description of Artificial Sequence: Synthetic Oligonucleotide

<400> SEQUENCE: 1
gcggccgcat ggtggtgtta aagctgtg          28

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic Oligonucleotide

<400> SEQUENCE: 2
gcggccgcta gtcatcatct tcatc          25

<210> SEQ ID NO 3
<211> LENGTH: 350
<212> TYPE: DNA
<213> ORGANISM: Glycine max
<220> FEATURE:
<221> NAME/KEY: CDS
<222> LOCATION: (9)..(320)
<220> FEATURE:
<221> NAME/KEY: mat_peptide
<222> LOCATION: (90)..(317)

<400> SEQUENCE: 3

```
gcggccgc atg gtg gtg tta aag gtg gtt tct tgg ttc ttt tcc ttg tgg      50
        Met Val Val Leu Lys Val Val Ser Trp Phe Phe Ser Leu Trp
                -25             -20             -15 ggg tta cta atg cgc gca tgg gaa ctg aac ctc ttc aaa agt gat cac       98
Gly Leu Leu Met Arg Ala Trp Glu Leu Asn Leu Phe Lys Ser Asp His
            -10              -5              -1   1 tca tca agt gat gat gag tct tca aaa cca tgc tgt gat ctc tgc atg     146
Ser Ser Ser Asp Asp Glu Ser Ser Lys Pro Cys Cys Asp Leu Cys Met
        5               10              15 tgc aca gcc tca atg cca cct caa tgc cat tgt gca gat att agg ttg     194
Cys Thr Ala Ser Met Pro Pro Gln Cys His Cys Ala Asp Ile Arg Leu
 20              25              30              35 aat tca tgt cac tca gct tgt gat cgc tgt gcg tgc aca cgc tcg atg     242
Asn Ser Cys His Ser Ala Cys Asp Arg Cys Ala Cys Thr Arg Ser Met
             40              45              50 cca ggc cag tgt cgt tgc ctt gac acc acc gac ttt tgc tac aaa cct     290
Pro Gly Gln Cys Arg Cys Leu Asp Thr Thr Asp Phe Cys Tyr Lys Pro
         55              60              65 tgc aag tcc agt gat gaa gat gat gac tag cggccgctgt tagtatatct       340
Cys Lys Ser Ser Asp Glu Asp Asp Asp
             70              75 taaattcttt                                                            350
```

<210> SEQ ID NO 4
<211> LENGTH: 103
<212> TYPE: PRT
<213> ORGANISM: Glycine max

```
<400> SEQUENCE: 4

Met Val Val Leu Lys Val Val Ser Trp Phe Phe Ser Leu Trp Gly Leu
 1               5                  10                  15

Leu Met Arg Ala Trp Glu Leu Asn Leu Phe Lys Ser Asp His Ser Ser
            20                  25                  30

Ser Asp Asp Glu Ser Ser Lys Pro Cys Cys Asp Leu Cys Met Cys Thr
        35                  40                  45

Ala Ser Met Pro Pro Gln Cys His Cys Ala Asp Ile Arg Leu Asn Ser
        50                  55                  60

Cys His Ser Ala Cys Asp Arg Cys Ala Cys Thr Arg Ser Met Pro Gly
65                  70                  75                  80

Gln Cys Arg Cys Leu Asp Thr Thr Asp Phe Cys Tyr Lys Pro Cys Lys
                85                  90                  95

Ser Ser Asp Glu Asp Asp Asp
            100
```

REDUCTION OF BOWMAN-BIRK PROTEASE INHIBITOR LEVELS IN PLANTS

This application claims the benefit of U.S. Provisional Application No. 60/097,450, filed Aug. 21, 1998.

FIELD OF THE INVENTION

This invention relates to a method for reducing Bowman-Birk protease inhibitor levels in plants using either co-suppression or antisense technology.

BACKGROUND OF THE INVENTION

Seeds of plants contain storage, or reserve, proteins which are synthesized during the development of the seeds. During germination and early seedling growth, these reserves are hydrolyzed to produce metabolic intermediates for use by the growing seedling. In harvested seeds, storage proteins represent an important nutritional source. The nutritional value of these seeds could be increased by altering the composition of the reserve proteins to decrease the amount of undesirable proteins in the seeds.

One major class of proteins found in the seeds of legumes are protease inhibitors which act as regulators of endogenous proteases and as proteins that protect plants from insect and pathogen attack.

Plant protease inhibitors are generally low molecular weight proteins, are characterized by the ability to combine with particular animal, and occasionally plant proteases, thereby abolishing the activity of these enzymes. Research suggests that active protease inhibitors may be toxic to humans and other animals, adversely affecting the nutritional quality of plant foodstuffs, even though they may be beneficial under other circumstances. Thus, there is a need to reduce the level of protease inhibitors in food.

Protease inhibitors are abundant in the legume family and constitute about 6% of the proteins of soybeans. Their antinutritional nature leads to pancreatic hyperplasia, acinar adenoma, and overall growth reduction when raw soybean meal is fed to monogastric animals, such as chicks, rats and quail.

Soybean (Glycine max) seed proteins are one example of storage proteins that are widely used in human foods such as infant formulas, tofu, soy protein isolates, soy flour, textured soy fibers and soy sauce. Soybean protein products serve as an excellent source of low cost, high quality protein for human needs. Soybeans are also widely used as a component of animal feeds. However, they must be properly processed to remove or deactivate protease inhibitors.

Soybean protease inhibitors are categorized into three classes: Kunitz trypsin inhibitors (KTi), Bowman-Birk inhibitors (BBi), and glycine-rich soybean trypsin inhibitors (GRSTi). The amino acid sequence of these inhibitors consists largely of sulfur-containing (methionine and cysteine) amino acids.

The major and predominantly expressed form of KTi is a 21.5 kDa protein which has inhibitory specificity for trypsin. BBi is a low molecular weight (8000 kDa) protein that inhibits both trypsin and chymotrypsin simultaneously at independent reactive sites. At least ten different isoforms of BBi have been reported. GRSTi are minor inhibitors of trypsin in soybean seed.

Various approaches have been taken to reduce the protease inhibitor content and/or activity of soybeans in order to improve the nutritional value of the grain. These include physical (heat) and chemical treatment of soy products, as well as genetic alteration of soybeans through conventional breeding techniques.

In any heat treatment, care must be taken because, even though heating is required to destroy the trypsin inhibitors, improper heating will decrease the nutritional value of the soybean protein itself. Furthermore, although the protease inhibitor activity is largely inactivated by denaturation through conventionally applied heat treatment of soy flour, 10–15% residual activity usually remains. The unusual structure of the BBi is the most likely reason for this residual activity. BBi is strongly cross-linked by disulfide bonds which gives the individual molecules resistance to heat denaturation. Thus, heat treatment of seed or soy products to reduce inhibitor expression is not completely successful and furthermore, is costly in energy usage. Furthermore, soy protein products often contain between 5% and 20% of the activity found in raw beans (Rackis, J. J.; Gumbmann, M. R., in Antinutrients and natural toxicants in food; Ory, R. L., ED.; Food and Nutrition Press; Westport, Conn., 1981, p 203) and there is a concern that this residual activity, due to non-denatured BBi, may be a significant health issue (Liener, I. E. (1986) J. Nutr. 116:920–923).

Another process used to eliminate protease inhibitors from raw soybeans is the solvent-extraction method. This chemical extraction, while removing the various inhibiting materials also results in considerable loss of the oil in the seed, thus, reducing its food value. At the same time, the solvent poses problems of cleanup and disposal.

Genetic modification of the soybean plant to develop low inhibitor activity varieties has also been proposed. However, this idea suffers from a number of drawbacks. Desirable nutritional value may be lost concomitantly with the reduction of the inhibitors. Cross pollination of the genetic variant with another cultivar could result in reexpression of the protease inhibitor gene. Further, altering expression of one inhibitor may not affect the expression of another. As yet, conventional breeding and tissue culture technology has been unable to produce a soybean plant with low levels of protease inhibitors although a need exists for such plants.

The need to reduce the protease inhibitor activity and the high cost of heat deactivation has led to the search of soybean germplasm accessions to find lines that lack the protease inhibitors. Isolines lacking KTi have been developed (Hymowitz, T. (1986) in Nutritional and Toxicological Significance of Enzyme Inhibitors in Foods, M. Friedman ed. Plenum Press. New York.). However, no nulls for BBi have been found in the 12,690 soybean accessions screened to date (Domagalski, J. M. et al. (1992) Crop Sci. 32:1502–1505). BBi nulls have been found in wild perennial Glycine species, however, these species are not traditionally used in a soybean breeding program due to hybridization problems and early pod abortion (Domagalski, J. M. et al. (1992) Crop Sci. 32:1502–1505).

Another approach taken to reduce the level of protease inhibitors in soybean is to purposely express the Brazil Nut storage protein. This protein is high in sulfur-containing amino acids, thus, its expression should limit the availability of this amino acids inhibiting the expression of the protease inhibitors which are also high in sulfur-containing amino acids (WO 95/27068). This method is thought to work because the pool of sulfur-containing amino acids common to both proteins is limiting during seed development. The expression of the new protein effectively competes for the limiting pool of sulfur-containing amino acids resulting in a reduction of the protease inhibitors. Although effective, there are some inherent limitations. Environmental conditions which favor increased sulfur reduction and synthesis of sulfur containing amino acids would cause inhibitor levels to rise. As growing conditions can not always be predicted, the tight control of inhibitor suppression needed for commercial success can not be guaranteed. Also, soybean breeders are trying to increase methionine and cysteine contents in seeds to improve their nutritional value. By doing so, they will select for lines with increased capacity to synthesize methionine and cysteine. This again, will lead to the breakdown of the suppression of the protease inhibitors. In addition, expression of novel high sulfur containing proteins, at levels required for suppression of the protease inhibitors, could lead to the introduction of a potentially new allergenic proteins in the soybean seeds, requiring special considerations for handling and labeling of protein products.

With the availability of KTi null line, genetic modification of soybean plants to develop lines with reduced levels of BBi is desirable. Not only would this decrease the heat required to deactivate protease inhibitor activity and lower residual activity in protein products on its own, but when bred with existing KTi null lines, one could create lines with very low overall protease activity.

BBi contains independent binding sites for both trypsin and chymotrypsin (Liener, I. E., in R. J. Summerfield and A. H. Bunting (eds), Advances in Legume Science, Royal Bot. Gardens, Kew, England). At least 10 isoforms of BBi have been purified from soybean seeds. However, several of the isoforms are related by proteolytic modification and it has been estimated that there are three subgroups of the inhibitor coded for by three independent genetic loci (Tan-Wilson et al. (1987) *J. Agric. Food. Chem.* 35:974–981). A search of GenBank for BBi sequences of Soybean (Glycine Max) identifies sequences for the classical BBi identified by Bowman and two isoforms designated C II and D II. These sequences are 73% and 83% identical and the encoded amino acid sequences are 57% and 75% identical to the sequences of the gene and protein of the Bowman isoform.

Thus, there remains a need to provide a novel method of eliminating BBi and its isoforms from soybean seeds using either co-suppression or antisense technology.

SUMMARY OF THE INVENTION

This invention concerns a method for reducing the level of a Bowman-Birk protease inhibitor in a plant which comprises
(a) transforming plant cells with a chimeric gene comprising a nucleic acid fragment encoding a Bowman-Birk protease inhibitor or a subfragment thereof or complement thereof which is operably linked to a promoter;
(b) growing fertile mature plants from the transformed plant cells obtained from step (a) to obtain seeds; and
(c) selecting from the seeds of step (b) those seeds containing reduced levels of the Bowman-Birk protease inhibitor when compared to plants not containing the chimeric gene.

Also of interest are plants produced by this method which contain reduced levels of a Bowman-Birk protease inhibitor as well as seeds obtained from such plants.

In still another aspect, this invention concerns crossing a plant produced by this method with a plant which is null for a Kunitz trypsin inhibitor and seeds obtained from such a plant.

In still a further aspect, this invention concerns a hybrid plant by crossing a plant made using the instant method with any other parental line wherein the resulting progeny contains in its genome a chimeric gene comprising a nucleic acid fragment encoding a Bowman-Birk protease inhibitor or a subfragment thereof or complement thereof which is operably linked to a promoter.

BRIEF DESCRIPTION OF THE FIGURES AND SEQUENCES

The invention can be more fully understood from the following detailed description and the Figure and Sequence Descriptions which form a part of this application.

The sequence descriptions summarize the Sequences Listing attached hereto. The Sequence Listing contains one letter codes for nucleotide sequence characters and the three letter codes for amino acids as defined in the IUPAC-IUB standards described in *Nucleic Acids Research* 13:3021–3030 (1985) and in the *Biochemical Journal* 219 (No. 2):345–373 (1984), and the symbols and format used for all nucleotide and amino acid sequence data further comply with the rules governing nucleotide and/or amino acid sequence disclosures in patent applications as set forth in 37 C.F.R. §1.821–1.825 and WIPO Standard St.25.

SEQ ID NOS:1 and 2 present the sequences of sense and antisense oligonucleotide primers that were used to amplify the CII isoform of BBi from soybean mRNA.

SEQ ID NO:3 sets forth the sequence of the PCR product that was obtained from soybean mRNA when the oligonucleotides of SEQ ID NOS:1 and 2 were used as primers.

SEQ ID NO:4 sets forth the sequence of the amino acid sequence of a BBi precursor protein derived from SEQ ID NO:3.

DETAILED DESCRIPTION OF THE INVENTION

In the context of this disclosure, a number of terms shall be utilized.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

The term "functionally equivalent subfragment thereof" refers to a portion or subsequence of the isolated nucleic acid fragment which does not affect the functional properties of the protein encoded by the nucleic acid fragment or does not affect the ability of the nucleic acid fragment to mediate alteration of gene expression by antisense or co-suppression technology.

The term "substantially similar" are used herein refers to nucleic acid fragments wherein changes in one or more nucleotide bases results in substitution of one or more amino acids, but do not affect the functional properties of the protein encoded by the DNA sequence. They also refer to nucleic acid fragments wherein changes in one or more nucleotide bases does not affect the ability of the nucleic acid fragment to mediate alteration of gene expression by antisense or co-suppression technology.

"Corresponding substantially" also refers to modifications of the nucleic acid fragments of the instant invention such as deletion or insertion of one or more nucleotides that do not substantially affect the functional properties of the resulting transcript vis-à-vis the ability to mediate alteration of gene expression by antisense or co-suppression technology or alteration of the functional properties of the resulting protein molecule. It is therefore understood as those skilled in the art will appreciate that the invention encompasses more than the specific exemplary sequences.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a gene which result in the production of a chemically equivalent amino acid at a given site, but do not effect the functional properties of the encoded protein, are well known in the art. For example, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the protein molecule would also not be expected to alter the activity of the protein. Each of the proposed modifications is well within the routine skill in the art, as is determination of retention of biological activity of the encoded products. Moreover, the skilled artisan recognizes that substantially similar nucleic acid sequences encompassed by this invention are also defined by their ability to hybridize, under moderately stringent conditions (1×SSC, 0.1% SDS, 55° C.), with the sequences exemplified herein.

A "substantial portion" of an amino acid or nucleotide sequence comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Altschul S. F. et al. (1993) *J. Mol. Biol.* 215:403–410) and Gapped Blast (Altschul S. F. et al. (1997) *Nucleic Acids Res.* 25:3389–3402).

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences. "Promoter" refers to a DNA sequence capable of controlling the expression of a coding sequence or functional RNA. The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". New promoters of various types useful in plant cells are constantly being discovered; numerous examples may be found in the compilation by Okamuro J. K and Goldberg R. B. (1989) *Biochemistry of Plants* 15:1–82. It is further recognized that since in most cases the exact boundaries of regulatory sequences have not been completely defined, DNA fragments of some variation may have identical promoter activity.

An "intron" is an intervening sequence in a gene that does not encode a portion of the protein sequence. Thus, such sequences are transcribed into RNA but are then excised and are not translated. The term is also used for the excised RNA sequences. An "exon" is a portion of the sequence of a gene that is transcribed and is found in the mature messenger RNA derived from the gene, but is not necessarily a part of the sequence that encodes the final gene product.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) *Molecular Biotechnology* 3:225).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht I. L. et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post transcriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the production of a functional end-product. Expression or overexpression of a gene involves transcription of the gene and translation of the mRNA into a precursor or mature protein. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. " Co-suppression" refers to the production of sense RNA transcripts capable of suppressing the expression of identical or substantially similar foreign or endogenous genes (U.S. Pat. No. 5,231,020).

"Altered expression" refers to the production of gene product(s) in transgenic organisms in amounts or proportions that differ significantly from that activity in comparable tissue (organ and of developmental type) from wild-type organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels M. J. (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel N. V. (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. The preferred method of corn cell transformation is use of particle-accelerated or "gene gun" transformation technology (Klein et al. (1987) *Nature (London)* 327:70–73; U.S. Pat. No. 4,945,050).

Standard recombinant DNA and molecular cloning techniques used herein are well known in the art and are described more filly in Sambrook, J., Fritsch, E. F. and Maniatis, T. *Molecular Cloning. A Laboratory Manual*; Cold Spring Harbor Laboratory Press: Cold Spring Harbor, 1989 (hereinafter "Sambrook").

"PCR" or "Polymerase Chain Reaction" is a technique for the synthesis of large quantities of specific DNA segments, consists of a series of repetitive cycles (Perkin Elmer Cetus Instruments, Norwalk, Conn.). Typically, the double stranded DNA is heat denatured, the two primers complementary to the 3' boundaries of the target segment are annealed at low temperature and then extended at an intermediate temperature. One set of these three consecutive steps is referred to as a cycle.

"Expression construct" is a plasmid vector comprising the instant chimeric gene can then be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis).

As used herein, "soybean" refers to the species *Glycine max, Glycine soja*, or any species that is sexually cross compatible with *Glycine max*. A "line" is a group of plants of similar parentage that display little or no genetic variation between individuals for a least one trait. Such lines may be created by one or more generations of self-pollination and selection, or by vegetative propagation from a single parent including tissue or cell culture techniques. "Germplasm" refers to any plant(s), line(s), or population of plants that has/have the potential to be used as parent(s) in a plant breeding program. The term "hybrid" refers to any offspring of a cross between two genetically unlike individuals (see Rieger R. et al. (1968) A Glossary of Genetics and Cytogenetics; Springer-Verlag: New York).

This invention relates to a method for reducing the level of a Bowman-Birk protease inhibitor in a plant which comprises (a) transforming plant cells with a chimeric gene comprising a nucleic acid fragment encoding a Bowman-Birk protease inhibitor or subfragment thereof or complement thereof which is operably linked to a promoter;

(b) growing fertile mature plants from the transformed plant cells obtained from step (a) to obtain seeds; and (c) selecting from the seeds of step (b) those seeds containing reduced levels of the Bowman-Birk protease inhibitor when compared to plants not containing the chimeric gene.

This invention also concerns transgenic plants produced by the instant method which contain reduced levels of a Bowman-Birk protease inhibitor as well as seeds obtained from such plants. As used herein, "plant" refers to either a whole plant, a plant part, a plant cell, or a group of plant cells. The class of plants which can be used in the method of the invention is generally as broad as the class of seed-bearing higher plants amenable to transformation, including both monocotyledonous and dicotyledonous plants which contain a Bowman-Birk protease inhibitor or a Bowman-Birk-like protease inhibitor, i.e, a protease inhibitor which is functionally comparable or equivalent to a Bowman-Birk protease inhibitor. Examples of such plants include, but are not limited to, soybean, wheat, corn, faba bean, alfalfa, cowpea, rice, peanut, barley and potato. Additional information can be found in the following references: For common bean, Wilson, K. A. and Laskowski, M. Sr. ((1975) *J. Biol. Chem.* 250: 4261–4267); for wheat, Odani, S. et. al. ((1986) *J. Biochem.* 100:975–983); for corn, Rohrmeier, T. and Lehle, L. ((1993) *Plant Mol. Biol.* 22:783–792); for faba bean, Asao, T. et al. ((1991) *J Biochem.* 110: 951–955); for alfalfa, Brown, W. E. et al. ((1985) *Biochemistry* 24:2105–2108); for cowpea, Morhy, L. and Ventura, M. M. ((1987) *An. Acad. Bras. Cienc.* 59:71–81); for rice, Tashiro, M. et al. ((1987) *J. Biochem.* 102:297–306); for peanut, Norioka, S. and Ikenaka, T. ((1983) *J. Biochem.* 94:589–599); for barley, Nagasue, A. et al. ((1988) *Agric. Biol. Chem.* 52:1505–1514 ); and for potato, Mitsumori, C. et al. ((1994) *Plant Mol. Biol.* 26:961–969).

Transformation techniques are well known to those skilled in the art of plant molecular biology. Methods of plant transformation include, but are not limited to, particle bombardment, microinjection, electroporation, and Agrobacterium-mediated DNA transfer.

The method of the invention utilizes a chimeric gene comprising a nucleic acid fragment encoding a Bowman-Birk protease inhibitor or subfragment thereof or complement thereof which is operably linked to a promoter wherein expression of the chimeric gene results in suppression of the Bowman-Birk protease inhibitor in the transformed host cell.

The nucleic acid fragment used in the construction of the chimeric gene corresponds substantially to the nucleotide sequence set forth in SEQ ID NO:3 or a subfragment thereof or complement of the nucleic acid fragment or subfragment thereof.

In another aspect, this invention concerns a plant produced by crossing a plant made using the method of the invention with a plant which is null for a Kunitz trypsin inhibitor (KTi) as well as seeds obtained from such plants.

The development of soybean lines with reduced levels of BBi will also facilitate the removal of almost all of the protease inhibitors in soybean via traditional plant breeding with crosses to existing Kti-null germplasm lines, i.e., plant lines that are null for a Kunitz trypsin inhibitor. Such double null lines will not only provide for savings in processing costs, but will also open up new feed markets, such as of "full-fat beans" for use in feeding to animals. Full-fat beans are not processed to remove the oil fraction and therefore have enhanced caloric value in feed. Also, without the need to heat or chemically denature BBi and KTi in protein products, storage proteins that comprise soy isolates or concentrates will remain in their native conformation resulting in functional properties that, up to now, are not possible using today's processing methods.

In still another aspect, this invention also concerns a hybrid plant obtained by crossing a plant obtained by the method of the invention with any other parental line wherein the resulting progeny contains in its genome a chimeric gene comprising a nucleic acid fragment encoding a Bowman-Birk protease inhibitor or a subfragment thereof or complement thereof which is operably linked to a promoter. Seeds obtained from such plants are also of interest.

EXAMPLE

The present invention is further defined in the following Example, in which all parts and percentages are by weight and degrees are Celsius, unless otherwise stated. It should be understood that this Example, while indicating preferred embodiments of the invention, is given by way of illustration only. From the above discussion and this Example, one skilled in the art can ascertain the essential characteristics of this invention, and without departing from the spirit and scope thereof, can make various changes and modifications of the invention to adapt it to various usages and conditions.

EXAMPLE

Soybean Plants with Reduced Levels of Bowman-Birk Inhibitor in Seeds

Using the cDNA sequence of the Bowman-Birk protease inhibitor C-II gene, obtained from the EMBL/GenBank/DDBJ database (Accession No. K01967), a pair of primers were designed SEQ ID NOS:1 and 2 and used in an RT-PCR (Geneamp□ RNA PCR Kit; Perkin Elmer Cetus, Norwalk, Conn.) reaction to obtain the complete C-II cDNA (SEQ ID NO:3) from total RNA extracts obtained from soybean cotyledons.

5'-GCGGCCGCATGGTGGTGTTAAAGCTGTG-3' [SEQ ID NO:1]

5'-GCGGCCGCTAGTCATCATCTTCATC-3' [SEQ ID NO:2]

Figure 1:
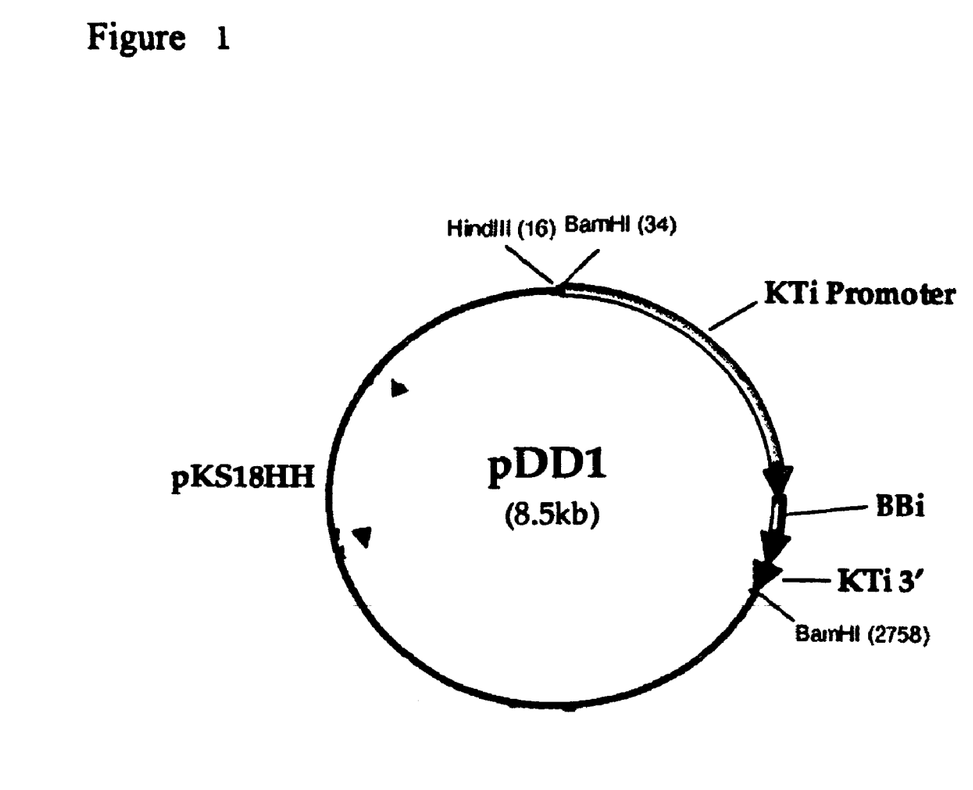
FIG. 1 is a map of the plasmid pDD1 containing a sense (cosuppression) construct of BBi isoform CII for use in suppressing levels of the protease inhibitor.

The resulting DNA fragment was separated by gel electrophoresis, isolated, and cloned at the Eco RV site of pGem-T using the pGem-T Vector System (Promega, Madison, Wis.) to create pGem-T/BBi. After determining the proper orientation of the insert for subsequent cloning, the BBi cDNA was isolated from the pGem-T/BBi plasmid and, using the Sph I and Sac I sites common to both DNAs, was directionally cloned into pZErO-1.1 (Invitrogen, San Diego, Calif.) yielding pZErO-1.1/BBi. To create an active transcriptional gene, the BBi cDNA was isolated from the pZErO-1.1/BBi plasmid using the restriction sites Xba I and Kpn I and, using the same sites, was directionally cloned into the plasmid pML70 (WO 94/11516 and WO 97/4773 1). This gave the plasmid pML70/BBi comprising an active transcriptional unit containing (i) the Kunitz trypsin inhibitor promoter (ii) the BBi C-II cDNA in sense orientation (iii) the Kunitz trypsin inhibitor 3' sequence. This transcriptional unit was released from pML70/BBi by restriction enzyme digestion using Bam HI. The DNA fragment was isolated using gel electrophoresis, and cloned into the Barm HI site of pKS18HH to make pDD1. The plasmid pKS18HH contains the following genetic elements: (i) T7 promoter/Hygromycin B Phosphotransferase (HPT)/T7 Terminator Sequence; (ii) 35S promoter from cauliflower mosaic virus (CaMV)/Hygromycin B Phosphotransferase (HPT)/Nopaline Synthase (NOS) 3' from Agrobacterium tumefaciens T-DNA; and (iii) plasmid vector pSP72 (Promega) with the β-lactamase coding region removed. Thus, the pKS18HH plasmid vector allows the use of Hygromycin B for selection in both E. coli and within our soybean transformation and regeneration system. Plasmid pDD1 (depicted in FIG. 1) was used to bombard somatic embryo tissue derived from soybean seeds.

Transformation of Somatic Embryo Cultures

Stock solutions and media used for transformation and propagation of soybean somatic embryos are described in WO 94/11516.

Soybean embryonic suspension cultures were maintained in 35 mL liquid media (SB172) on a rotary shaker (150 rpm) at 28° C. with a mix of fluorescent and incandescent lights providing a 16 h day 8 h night schedule. Cultures were subcultured every 2 weeks by inoculating approximately 35 mg of tissue into 35 mL of liquid media.

Soybean embryonic suspension cultures were transformed with pDD1 by the method of particle gun bombardment (see Klein et al. (1987) *Nature* 327:70). A DuPont Biolistic™ PDS1000/He instrument was used for these transformations.

Five μL of pDD1 plasmid DNA (1 μg/μL), 50 μL CaCl$_2$ (2.5 M), and 20 μL spermidine (0.1 M) were added to 50 μL of a 60 mg/mL 1.0 μm or 0.6 μm gold particle suspension. The particle preparation was agitated for 3 minutes, spun in a microfuge for 10 seconds and the supernatant removed. The DNA-coated particles were then washed once with 400 μL 100% ethanol and resuspended in 40 μL of anhydrous ethanol. The DNA/particle suspension was sonicated three times for 1 second each. Five μL of the DNA-coated gold particles were then loaded on each macro carrier disk.

Approximately 200 to 600 mg of two-week-old suspension culture was placed in an empty 60 mm×15 mm petri dish and the residual liquid removed from the tissue using a pipette. The tissue was placed about 3.5 inches away from the retaining screen and bombarded twice. Membrane rupture pressure was set at 1100 psi and the chamber was evacuated to −28 inches of Hg. Two plates were bombarded per construct per experiment. Following bombardment, the tissue was divided in half, placed back into liquid media, and cultured as described above.

Four to six days after bombardment, the liquid media was exchanged with fresh SB172 containing 50 mg/mL hygromycin. The selective media was refreshed weekly. Six weeks after bombardment, green, transformed tissue was isolated and inoculated into flasks to generate new transformed embryonic suspension cultures.

Transformed embryonic clusters were removed from liquid culture media and placed on a solid agar media, SB103, plus 0.5% charcoal to begin maturation. After 1 week, embryos were transferred to SB103 media minus charcoal. After 3 weeks on SB103 media, maturing embryos were separated and placed onto SB148 media. Conditions during embryo maturation were 26° C., with a mix of fluorescent and incandescent lights providing a 168 h day 8 h night schedule. After 6 weeks on SB148 media, embryos were analyzed for the expression of the β-conglycinin subunit proteins. Each embryonic cluster gave rise to 5 to 20 somatic embryos. Fertile plants were regenerated from the embryos as described in WO 94/11516.

Detection of BBi

Detection of BBi was carried out by conventional immunoblot (western) methods. For analysis of both somatic embryos and seeds, 8 μL of (2×) loading buffer was added to 8 μL of sample extract. The (2×) loading buffer consisted of 100 mM Tris-HCl (pH 7.5), 4% SDS, 0.2% bromophenol blue, 15% glycerol, and 200 mM βME. The mixture was heated at 95° C. for 4 minutes. Sample mixes were then microfuged (12,000 rpm for 20 seconds) and loaded onto a 10% precast Ready Gel™ (Bio-Rad, Richmond, Calif.) that was assembled into a mini-Protein 11 Electrophoresis Cell (Bio-Rad). Bio-Rad Tris/Glycine/SDS Buffer was used as the running buffer and voltage was a constant 125V. In addition to sample extracts, each gel contained one lane with a molecular weight standard (Bio-Rad SDS-PAGE standard, low range) and one lane of either soybean seed protein extracted from commercial defatted soy flour, or BBi standard protein obtained from Sigma Chemical Co. Following electrophoresis, the proteins were electrophoretically transferred to the nitrocellulose membrane from the gel support (SDS-Page) using the Mini Trans-Blot Electrophoretic Transfer Cell (Bio-Rad). Transfers were done in Buffer: 25 mM Tris, 192 mM glycine, 20% v/v methanol, pH 8.3. Transfers were run overnight at 25 Volts. After transfer, the nitrocellulose blots were rinsed for 10 minutes in TBS Buffer (TBS: 20 mM Tris, 500 mM NaCl, pH 7.5). The blots were then immersed in blocking solution (5% nonfat dry powdered milk in TBS buffer), the solution gently agitated using an orbital shaker platform, and incubated for 30 minutes to 1 h at room temperature (RT). The blocking solution was then poured off, TTBS (0.05% Tween-20 concentration in TBS) was added, and allowed to wash for 5 minutes with gentle agitation at RT. This step was repeated twice. After washing, the BBi antibody was added to the membrane and incubated 1 to 2 h with gentle agitation at RT. The antibody was diluted 1:5000 in antibody buffer (1% milk in TTBS). Antisera was prepared by Covance Research Products, Inc. P.O. Box 7200, Denver, Pa. 17517 by injecting Elite rabbits with BBi protein (1.0 mg/ml) to yield a Bowman-Birk Inhibitor protein-specific antibody. The unbound BBi antibody was removed from the membranes by washing three times in TTBS for 5 minutes at RT. The membrane was then incubated for 1 to 2 h at RT in antibody buffer with 1:2000 horseradish peroxidase-linked donkey anti-rabbit Ig (Amersham Life Science). To remove the excess secondary antibody, the membrane was washed three times for 5 minutes in TTBS. Detection was done using the ECL Western blotting protocol (Amersham Life Science) using detection reagents 1 and 2. Equal volumes of bottle 1 and bottle 2 were mixed to give a solution sufficient to cover the membranes. The membrane blots were incubated in detection solution for 1 minute with gentle rocking motion. The excess solution was drained off and the membranes were placed, protein side up, in film cassettes to expose to autoradiography film (Kodak Scientific Imaging Film X-OMAT AR) for 1 minute.

Analysis of Transformed Somatic Embryos

Initial experiments were performed to determine the time during the development of somatic embryos when BBi could first be detected. Cotyledons of non-transformed embryos (generated as above, except they did not undergo bombardment) were dissected from embryos 5, 7, and 9 weeks after initiating maturation and kept frozen at −80° C. until analyzed Cotyledon tissue was weighed, extraction buffer was added at 10 μL/mg tissue, and that tissue ground using a Pellet Pestle Disposable Mixer (Kimble/Kontes). Extraction buffer consisted of 50 mM Tris-HCl (pH 7.5), 10 mM β-mercaptoethanol (BME), and 0.1% SDS. The samples were then microfuged at 12,000 rpm for 10 minutes and the supernatant removed by pipette to a new microfuge tube. Extracts were kept frozen at −20° C. until used. From these initial experiments it was determined that BBi could be detected as early as five weeks after initiation of maturation.

Twenty-seven clones were recovered from hygromycin selection. Analysis of transformed embryos was carried out at 5 to 7 weeks after the start of maturation using the method described above. Five clones produced transgenic embryos with significantly reduced, or undetectable levels of BBi (Table 1). These embryos are indicated by the highlighted rows.

TABLE 1

Analysis of Transgenic Somatic Embryos

| Bombardment experiment | Plate # | Clone | Number of Embryos | Strong Band | BBi Band Intensity Significantly Reduced | Not Detectable |
|---|---|---|---|---|---|---|
| 2048 | 1 | 1 | 6 | 5 | 1 | 0 |
| 2048 | 2 | 1 | 5 | 5 | 0 | 0 |
| 2048 | 2 | 2 | 6 | 0 | 3 | 3 |
| 2048 | 2 | 3 | 6 | 6 | 0 | 0 |
| 2048 | 3 | 1 | 6 | 6 | 0 | 0 |
| 2048 | 4 | 1 | 6 | 0 | 6 | 0 |
| 2048 | 4 | 2 | 6 | 6 | 0 | 0 |
| 2048 | 4 | 3 | 5 | 0 | 3 | 2 |
| 2048 | 4 | 3 | 10 | 8 | 0 | 2 |
| 2048 | 5 | 1 | 6 | 6 | 0 | 0 |
| 2048 | 5 | 2 | 6 | 4 | 2 | 0 |
| 2048 | 5 | 4 | 9 | 0 | 0 | 9 |
| 2048 | 5 | 5 | 6 | 6 | 0 | 0 |
| 2048 | 5 | 7 | 6 | 6 | 0 | 0 |
| 2048 | 5 | 8 | 6 | 4 | 1 | 1 |
| 2048 | 5 | 9 | 6 | 6 | 0 | 0 |
| 2048 | 5 | 9 | 6 | 6 | 0 | 0 |
| 2048 | 5 | 10 | 6 | 6 | 0 | 0 |
| 2048 | 6 | 1 | 6 | 0 | 0 | 6 |
| 2048 | 6 | 3 | 6 | 6 | 0 | 0 |
| 2048 | 6 | 4 | 6 | 6 | 0 | 0 |
| 2048 | 6 | 5 | 3 | 3 | 0 | 0 |
| 2048 | 8 | 2 | 6 | 6 | 0 | 0 |
| 2041 | 1 | 1 | 5 | 2 | 3 | 0 |
| 2041 | 3 | 1 | | | | |
| 2041 | 4 | 1 | 5 | 5 | 0 | 0 |
| 2041 | 4 | 2 | 5 | 5 | 0 | 0 |

Wild Type

| Jack | | | | 6 | 6 | 0 | 0 |
| 898 9254 | | | | 6 | 6 | 0 | 0 |

Figure 2:
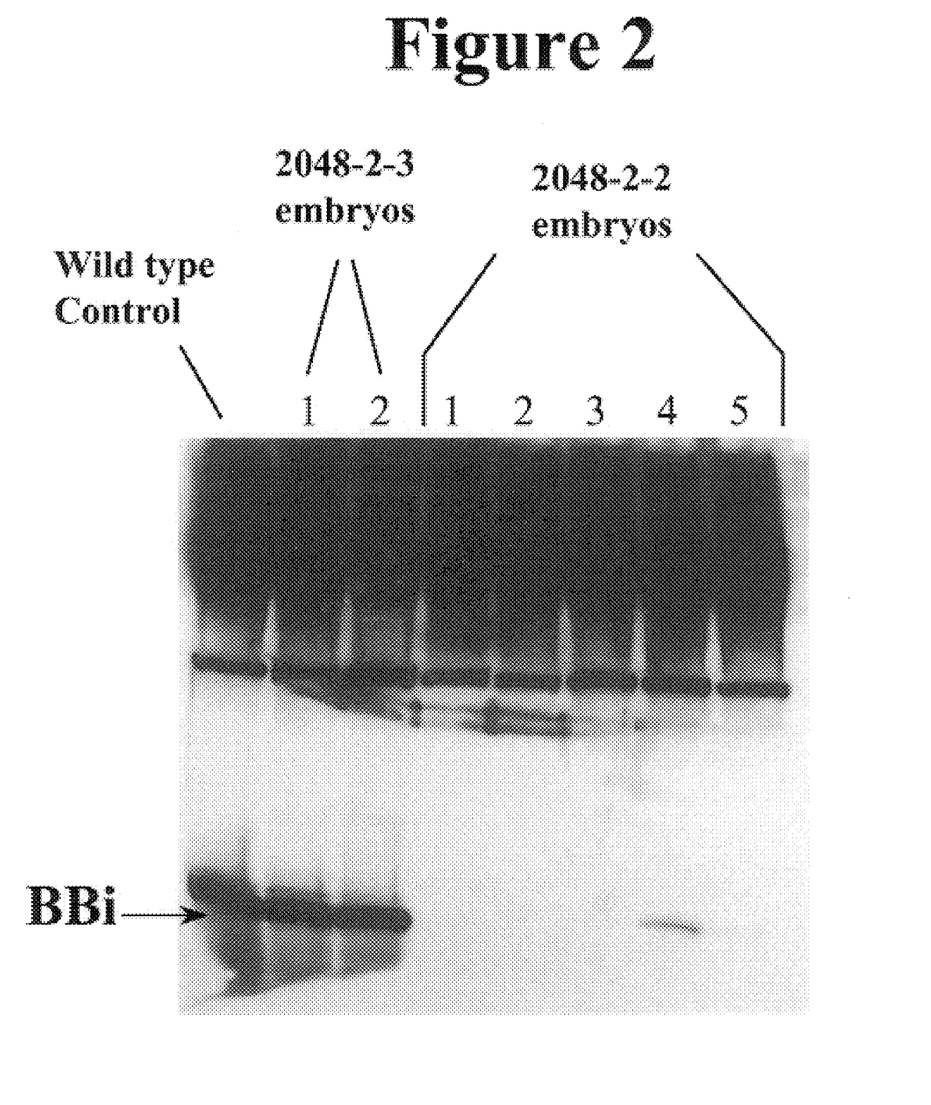
FIG. 2 depicts the result of Western analysis of the expression of BBi in embryos from wild-type plants, vector control transformed plant tissue and from somatic embryos transformed with pDD 1.

FIG. 2 shows a representative western for the analysis of the transgenic somatic embryos. A large band corresponding to BBi is detected in tissues from wild type control and from embryos derived from the event 2048-2-3 while very little or no BBi is detected in tissue from embryos derived from the event 2048-2-2. Somatic embryos of clones suppressing the expression of BBi were germinated and regenerated into plants.

Analysis of Transgenic Seed

Figure 3:
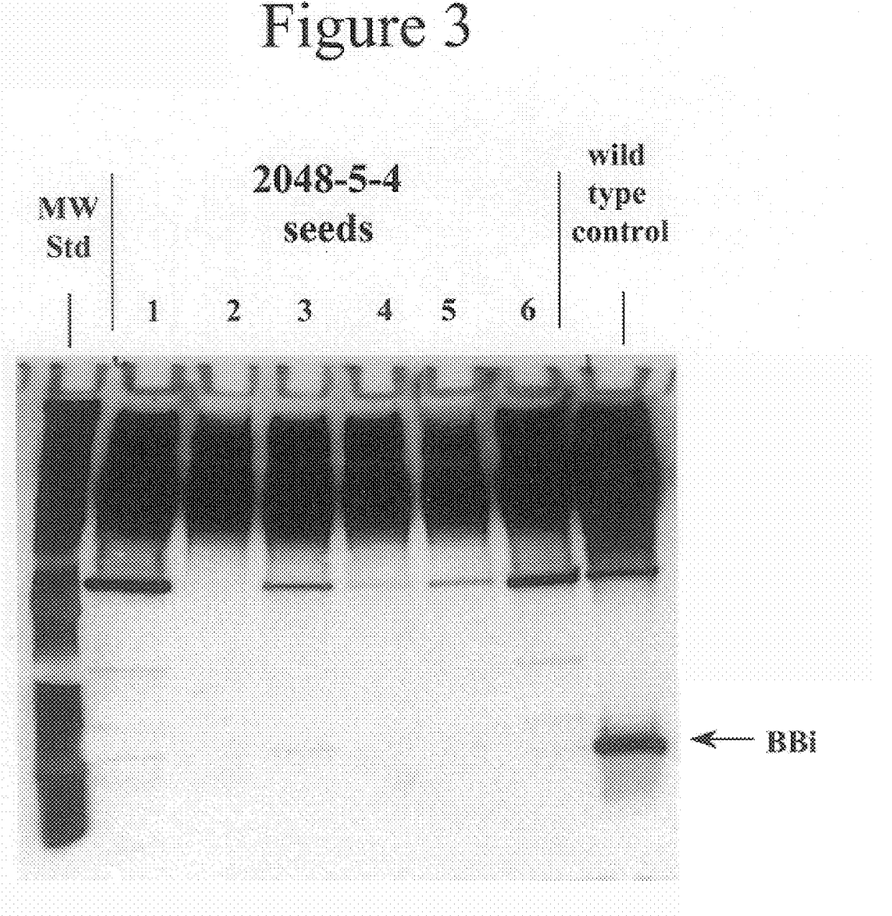
FIG. 3 depicts the result of Western analysis of the expression of BBi in seeds obtained from wild-type plants and from and plants transformed with pDD 1.

Seed chips, weighing approximately 10 mg, were taken from R0:1 seeds of transgenic plants regenerated from the event 2048-5-4 and analyzed for the presence of BBi using the methods described above. Of the sixty four seeds analyzed, 18 were found to have BBi levels below the detection levels. Another 12 seeds were found to have significantly reduced levels. FIG. 3 shows a representative western (conducted as described above) for the analysis of the transgenic seed. Samples loaded in lanes labeled 3 and 6 have significantly reduced levels of BBi while the levels of BBi in the samples loaded in the remaining lanes are below the detection limits.

These data clearly demonstrate the effectiveness of pDD1 in mediating a cosuppression effect on the level of BBi in embryos and in seeds generated from tissue transformed with the plasmid.

What is claimed is:

1. A method for reducing the level of a Bowman-Birk protease inhibitor in a plant which comprises
   (a) transforming plant cells with a chimeric gene comprising a nucleic acid fragment having a sequence identity of at least 75% when compared to a nucleic acid sequence as set forth in SEQ ID NO:3 or a complement thereof which is operably linked to a promoter;
   (b) growing fertile mature plants from the transformed plant cells obtained from step (a) to obtain seeds; and
   (c) selecting from the seeds of step (b) those seeds containing reduced levels of the Bowman-Birk protease inhibitor when compared to plants not containing the chimeric gene.

2. The method of claim 1 wherein said nucleic acid fragment comprises the nucleotide sequence set forth in SEQ ID NO:3 or a functionally equivalent subfragment thereof.

3. The method of claim 1 wherein the plant cells are selected from the group consisting of soybean, wheat, corn, faba bean, alfalfa, cowpea, rice, peanut, barley and potato.

4. A plant produced by the method of claim 1 wherein the plant comprises in its genome a chimeric gene comprising a nucleic acid sequence having a sequence identity of at least 75% when compared to a nucleic acid sequence as set forth in SEQ ID NO:3 or complement thereof which is operably linked to a promoter and further wherein the plant comprises a reduced level of a Bowman-Birk protease inhibitor when compared to a non-transformed plant.

5. Seeds obtained from the plant of claim 4 wherein the seeds comprise in their genome a chimeric gene comprising a nucleic acid sequence having a sequence identity of at least 75% when compared to a nucleic acid sequence as set forth in SEQ ID NO:3 or complement thereof which is operably linked to a promoter.

6. A plant produced by crossing the plant of claim 4 with a plant which is null for a Kunitz trypsin inhibitor wherein the plant comprises in its genome a chimeric gene comprising a nucleic acid sequence having a sequence identity of at least 75% when compared to a nucleic acid sequence as set forth in SEQ ID NO:3 or complement thereof which is operably linked to a promoter.

7. Seeds obtained from the plant of claim 6 wherein the seeds are null for a Kunitz trypsin inhibitor and said seeds comprise in their genome a chimeric gene comprising a nucleic acid sequence having a sequence identity of at least 75% when compared to a nucleic acid sequence as set forth in SEQ ID NO:3 or complement thereof which is operably linked to a promoter.

8. A hybrid plant obtained by crossing the plant of claim 4 with any other parental line wherein the resulting progeny contains in its genome a chimeric gene comprising a nucleic acid fragment encoding a Bowman-Birk protease inhibitor or a subfragment thereof or complement thereof which is operably linked to a promoter.

9. Seeds obtained from the plant of claim 8 wherein the seeds comprise in their genome a chimeric gene comprising a nucleic acid sequence having a sequence identity of at least 75% when compared to a nucleic acid sequence as set forth in SEQ ID NO:3 or complement thereof which is operably linked to a promoter.

* * * * *